United States Patent
Evans et al.

(10) Patent No.: US 6,887,824 B1
(45) Date of Patent: May 3, 2005

(54) DIVALENT LANTHANIDE REDUCTION CATALYSTS

(75) Inventors: William J. Evans, Mission Viejo, CA (US); Nathan T. Allen, Stow, OH (US)

(73) Assignee: The Regents of the University of California, Oakland, CA (US)

( * ) Notice: Subject to any disclaimer, the term of this patent is extended or adjusted under 35 U.S.C. 154(b) by 105 days.

(21) Appl. No.: 10/088,749

(22) PCT Filed: Sep. 18, 2000

(86) PCT No.: PCT/US00/25520

§ 371 (c)(1),
(2), (4) Date: Aug. 8, 2002

(87) PCT Pub. No.: WO01/21667

PCT Pub. Date: Mar. 29, 2001

Related U.S. Application Data (60) Provisional application No. 60/155,310, filed on Sep. 21, 1999.

(51) Int. Cl.[7] .............................. B01J 23/10; C08F 4/72

(52) U.S. Cl. ...................................... 502/302; 526/164
(58) Field of Search ........................... 526/164; 502/302

(56) References Cited

PUBLICATIONS

Bochkarev et al., Synthesis and Structure of the First Molecular Thullium (II) Complex: TmI2(DME)3, Angew. Chem. Int. Ed. Engl. 1997, 36, No. 1/2.*
Brunetti et al., J. Chem. Eng. Data 1999, 44, 509–515.*
Evans, Coordination Chemistry of Samarium Diiodide with Ethers . . . , J. Am. Chem. Soc. 1995, 117 8999–9002.*

* cited by examiner

*Primary Examiner*—Robert D. Harlan
(74) *Attorney, Agent, or Firm*—Robert D. Buyan; Stout, Uxa, Buyan & Mullins, LLP (57) ABSTRACT

The present invention relates generally to the chemistry of inorganic reduction catalysts, and more particularly to the composition and use of dihalogenated lanthanides catalysts, for example $TmI_2$ or $DyI_2$, to facilitate reduction reactions such as the preparation of alkylated hydrocarbons and/or organic polymers.

63 Claims, 3 Drawing Sheets

DIVALENT LANTHANIDE REDUCTION CATALYSTS

RELATED APPLICATION

This application claims priority to U.S. Provisional Patent Application Ser. No. 60/155,310, filed on Sep. 21, 1999.

This invention was made with Government support under Grant No. 9815151, awarded by the National Science Foundation. The Government has certain rights in this invention.

FIELD OF INVENTION

The present invention relates generally to the chemistry of inorganic reduction catalysts, and more particularly to the composition and use of dihalogenated lanthanides catalysts to facilitate reduction reactions such as the preparation of alkylated hydrocarbons and/or organic polymers.

BACKGROUND

Early studies of lanthanide reagents simply sought to develop reactivity patterns mimicking those of more established organolithium or Grignard reagents. However, as the complexity of organic molecules requiring synthesis increased, demands for more highly selective reagents heightened accordingly. Consequently, the search for reagents which would complement those of the traditional organometallic nucleophiles brought more serious attention to the lanthanides, and an explosive expansion in the application of lanthanide reagents to organic synthesis began.

The perception that lanthanide metals are rare and therefore inaccessible or expensive may be a contributing factor to their long-lasting neglect and slow development as useful synthetic tools. In fact, "rare earths" in general are relatively plentiful in terms of their abundance in the earth's crust. Modem separation methods have made virtually all of the lanthanides readily available in pure form at reasonable cost.

It may be the special combination of inherent physical and chemical properties of the lanthanides that set them apart from all other elements, and provides a unique niche for these elements and their derivatives in selective organic synthesis. The lanthanides as a group are quite electropositive, for example electronegativities of samarium and ytterbium are 1.07 and 1.06, respectively, on the Allred-Rochow scale, and the chemistry of these elements is predominantly ionic. This may be because the 4f-electrons do not have significant radial extension beyond the filled $5s^2 5p^6$ orbitals of the xenon inert gas core. The lanthanides therefore behave as close-shell inert gasses with a tripositive charge, and in general electrostatic and steric interactions play a greater role in chemistry of the lanthanides than do interactions between the metal and associated ligand orbitals.

Compared with transition metals, the ionic radii of the lanthanides are large. Most transition metal ionic radii lie in the range from 0.6 to 1.0 Å, whereas the lanthanides have an average ionic radius of approximately 1.2 Å. Divalent species are, of course, even larger, eight-coordinate SmII has an ionic radius of 1.41 Å, for example. The relatively large ionic radii of the lanthanides allow the accommodation of up to 12 ligands in the coordination sphere, and coordination numbers of seven, eight and nine are common. Owing to the well known lanthanide contraction, ionic radii decrease steadily across the row of lanthanides in the periodic table. The lanthanide contraction may be a consequence of poor shielding of the 4f-electrons, resulting in an increase effective nuclear charge and a concomitant decrease in ionic radius. As expected, higher coordination numbers are most common in the larger, early lanthanides.

According to the concept of hard and soft acids and bases (HSAB) established by Pearson, lanthanide +3 ions are considered to be hard acids, falling between Mg(II) and Ti(IV) in the established scale. Lanthanides therefore complex preferentially to hard bases such as oxygen donor ligands.

The strong affinity of lanthanides for oxygen is further evidenced by the bond dissociation energies for the gas phase dissociation of diatomic lanthanide oxides (LnO). For example, although they are among the lowest values for lanthanides, both SmO (136 kcal/mol; 1 cal=4.18J) and Yb (95 kcal/mol) exhibit values significantly higher than that for MgO (86 kcal/mol). This demonstrates oxophilicity (strong metal-oxygen bonds and hard Lewis acid character) has been used to great advantage in organic synthesis. These properties have been exploited extensively to enhance carbonyl substrate reactivity, and also control stereochemistry in carbonyl addition reactions through chelation. Of particular significance is the exploitation of the lanthanide(II). To date, this important divalent state involves only three metals: Eu(II), Yb(II) and Sm(II).

Although the use of Eu(II), Yb(II) and Sm(II) is quite popular, there exist many drawbacks. For example, samarium diiodide, or its complex $SmI_2$ (tretrahydrofuran (THF))$_x$, has become a popular reducing agent in organic synthesis. It may be used under a variety of conditions as a reducing agent to accomplish a wide range of transformations. However, in many cases the reducing power of $SmI_2$ or $SmI_2(THF)_x$ needs to be enhanced by the addition of, for example, hexamethylphosphoramide (HMPA). Unfortunately, this most effective and popular additive may be highly carcinogenic and alternatives are highly desirable. Several other methods for increasing $SmI_2$ reactivity have been reported and include the addition of transition metal salts or samarium metal, photolysis, and the design of intramolecular reactions. However, such methods of enhancing $SmI_2$ reactivity remain inadequate.

There is a need for the identification, synthesis and development of new lanthanide reducing agents which are more reactive than that of Eu(II), Yb(II) and Sm(II).

SUMMARY OF THE INVENTION

The present invention provides new divalent lanthanide reducing agents and methods for using such reducing agents.

In accordance with the invention, there is provided a method of reducing a compound to form a reduction product, such method generally comprising the step of combining the compound with a divalent lanthanide reducing agent of General Formula A, as follows:

wherein;

M is a lanthanide other than the Europium, Ytterbium or Samarium;

$G_1$ and $G_2$ may be the same or different chemical entity independently selected from a halogen, alkyl, aryl, $NR_2$, $OR_2$, $PR_2$, or SR; wherein N is a nitrogen, O is an oxygen, P is a phosphorus and R is selected from the group consisting of an alkyl, an aryl, and a cycloalkyl from about 1 to about 20 carbon atoms.

Further in accordance with the invention, M may be Thulium, Dysprosium, Neodymium, Cerium, Praseodymium, Gadolinium, Terbium, Holmium, Erbium, Lutetium, Lanthanum or Yttrium.

Still further in accordance with the invention, $G_1$ and $G_2$ may be the same halogen, for example Iodine; or alternatively $G_1$ and $G2$ may be different halogens, such as Iodine and Chlorine (or Bromine).

Still further in accordance with the invention, there is provided an embodiment wherein the divalent lanthanide reduction catalyst is thulium diiodide.

Still further in accordance with the invention, there is provided an embodiment wherein the divalent lanthanide reduction catalyst is Dysprosium diiodide.

Still further in accordance with the invention, a compound of formula A may be combined with a solvent (S), such that coordinate bond(s) are formed between the lanthanide M molecules and the solvent S molecules. The solvent S may be a Lewis base, for example: an ether (e.g. a di-alkyl-oxy-ethane), a furan (e.g. tetrahydrofuran), a diene (e.g. butadiene), a nitrile (e.g. acetonitrile) and other heteroatom donor bases. The complex formed by the combination of the lanthanide M and solvent S may have the General Formula B, as follows:

wherein;

M is a lanthanide other than the Europium, Ytterbium or Samarium;

$G_1$ and $G_2$ may be the same or different chemical entity independently selected from a halogen, alkyl, aryl, $NR_2$, $OR_2$, $PR_2$, or SR; wherein N is a nitrogen, O is an oxygen, P is a phosphorus and R is selected from the group consisting of an alkyl, an aryl, and a cycloalkyl from about 1 to about 20 carbon atoms; and, S is dimethoxyethane (DME).

Any feature or combination of features described herein are included within the scope of the present invention provided that the features included in any such combination are not mutually inconsistent.

Additional advantages and aspects of the present invention will become apparent to those of skill in the art upon reading and understanding the detailed description and examples of specific embodiments set forth herebelow.

DETAILED DESCRIPTION

In a broad embodiment, the invention provides for a method of reducing a compound to form a reduction product. The compound according to this invention is preferably a reducible molecule, such as those containing at least one multiple bond, for example a carbon-carbon double bond, a carbon-carbon triple bond or a carbonyl in a cyclic or acyclic structure. The cyclic or acyclic structure optionally contains one or more heteroatoms. In one embodiment, the compound according to this invention is an arene. The method comprises the step of combining the compound with a lanthanide catalyst, having General Formula A:

wherein;

M is a lanthanide other than the Europium, Ytterbium or Samarium;

$G_1$ and $G_2$ may be the same or different chemical entity independently selected from a halogen, alkyl, aryl, $NR_2$, $OR_2$, $PR_2$, or SR; wherein N is a nitrogen, O is an oxygen, P is a phosphorus and R is selected from the group consisting of an alkyl, an aryl, and a cycloalkyl from about 1 to about 20 carbon atoms.

In a preferred embodiment, $G_1$ and $G_2$ are halogens, $G_1$ being the first halogen and $G_2$ being the second halogen. In one embodiment, $G_1$ and $G_2$ are the same halogen, for example Iodine. In another embodiment, $G_1$ and $G_2$ are different halogens, for example $G_1$ may be an Iodine and $G_2$ may be a Bromine or a Chlorine.

In one broad embodiment, a lanthanide catalyst may be employed to affect an alkylation of the compound to form an alkylated organic compound, which is a reduction product. Preferably, the alkylated organic compound is a pharmaceutical compound, especially because unlike many of their main group and transition metal counterparts, inorganic lanthanide compounds are generally classified as nontoxic when introduced orally. For example, samarium chloride and ytterbium chloride exhibit similar toxicity to that of sodium chloride ($LD_{50}$ of >2000–6700 mg/kg in mice versus 4000 mg/kg for NaCl). Although toxicity may obviously vary to some extent based on the ligands attached to the metal, in most cases lanthanide complexes are converted to hydroxides immediately on ingestion, and thus have limited absorption through the digestive tract. Moderate toxicity may be exhibited by lanthanide salts introduced via the intraperitoneal route. As such, the prospect of using lanthanide as a catalyst in the synthesis of pharmaceuticals for use in mammals, including human, is very attractive.

The alkylation process may follow the general scheme:

wherein R may be an alkyl group and J may be a halogen, for example Iodine, fluorine, preferably Bromine or Chlorine; R' is the organic compound and RR' is the alkylated organic compound.

In a preferred embodiment, the lanthanide catalyst in the alkylation process may include a Thulium diiodide. Moreover, the lanthanide catalyst may include a Thulium diiodide $(DME)_3$.

Recently, in collaboration with the Bochkarev group, we reported the synthesis and structure of the first molecular Tm(II) complex, $TmI_2(DME)_3$. This complex is found to be structurally analogous to samarium diiodide in DME, but it is much more reactive since $4f^{13}$ Tm(II) has a much greater reduction potential than $4f^6$ Sm(II). However, preliminary studies indicate that this compound is so reactive, that it is uncertain if this species would be useful as a reagent like $SmI_2(THF)_x$ in organic transformations.

To determine if $TmI_2(DME)_x$ is viable as a reagent and if it has utility as an alternative for $SmI_2(THF)_x$/HMPA, we examine its reactivity in the coupling of 4-tert-butylcyclohexanone with alkyl halides, Scheme 1. $TmI_2(DME)_x$ has x=3 when obtained as single crystals from DME and x=2 when obtained as a powder. This is similar to $SmI_2(THF)_x$ which has x=5 as single crystals and x=2 as a powder. See Evans, W. J.; Gummersheimer, T. S.; Ziller, J.

W. J. *Am. Chem. Soc.*, 1995, 35, 8999–9002. The powder form, $TmI_2(DME)_2$, can be produced by reduction of a suspension of $TmI_3(DME)_2$ (2.5 g, 3.4 mmol) in 50 mL of oxygen-free, dry DME with Tm powder (0.65 g, 3.86 mmol). The reaction is heated to reflux under nitrogen for 40 minutes and is filtered to remove unreacted Tm metal. Removal of the solvent under vacuum, leads to quantitative conversion to $TmI_2(DME)_2$ (3.07 g, 5.1 mmol) as an emerald green powder.

This reaction is used as an assay, since it has been thoroughly studied with samarium diiodide. Reactions are carried out in accordance with the samarium Grignard procedure introduced by Curran et al., in which two equivalents of the lanthanide reagent are added to the alkyl halide and the ketone is added subsequently. Reactions using $SmI_2(THF)_x$/HMPA are conducted to insure that Sm/Tm comparisons could be made under one uniform set of conditions.

As shown in Table 1, $SmI_2(THF)_x$/HMPA gives yields and selectivities for the reaction of phenethyl iodide with 4-tert-butylcyclohexanone under our conditions which are consistent with those in the literature (entry 1). $TmI_2(DME)_x$ in DME matches these results (entry 2), but without any HMPA present. In comparison, $SmI_2(THF)_x$ in the absence of HMPA is reported to reduce iodides only after extended reaction times in refluxing THF.

After establishing that HMPA-free $TmI_2(DME)_x$ is at least equivalent to $SmI_2(THF)_x$/HMPA, less reactive halides are examined. Reactions with alkyl bromides and $SmI_2(THF)_x$/HMPA are reported to occur, but at a much slower rate than iodides. In our control reactions with 2-phenethyl bromide (entry 3), $SmI_2(THF)_x$/HMPA required 15 minutes to change color from the deep purple of Sm(II) to an orange-yellow characteristic of Sm(III). After the addition of 4-tert-butylcyclohexanone, a 65% conversion to α-4-tert-butyl-1-phenethyl-cyclohexanol and β-4-tert-butyl-1-phenethyl-cyclohexanol in a 77:23 ratio is found. In contrast, when 2-phenethyl bromide is added to $TmI_2(DME)_x$ (entry 4), an immediate color change from the emerald green Tm(II) solution to a bright yellow occurred. A white/gray precipitate forms concurrently which is consistent with the formation of $TmI_3$. After addition of the ketone, a 92% conversion to α-4-tert-butyl-1-phenethyl-cyclohexanol and β-4-tert-butyl-1-phenethyl-cyclohexanol in a 79:21 ratio is observed.

The difference between the Tm and Sm diiodide reagents is even more pronounced with 2-phenethyl chloride. When $SmI_2(THF)_x$/HMPA (entry 5) is employed, little color change is observed, even after 18 hours at 25° C. After addition of the ketone, no product is formed. This is consistent with literature reports that unactivated chlorides are not very reactive with samarium diiodide unless some type of enhancement is employed e.g. the addition of catalytic amounts of $NiX_2$, reaction in the presence of samarium metal at 67° C. for 20 h, photolysis for 3–9 h at 25–40° C.,[9] or an intramolecular reaction.[10] However, $TmI_2(DME)_x$ in DME (entry 6) reacts to give a yellow solution in 3 minutes, which after addition of the ketone results in a 79:21 ratio of α-4-tert-butyl-1-phenethyl-cyclohexanol and β-4-tert-butyl-1-phenethyl-cyclohexanol in 88% yield.

Since solvent effects can be influential in $SmI_2(THF)_x$ reductions, a comparison of the effect of ethereal solvents on the lanthanide diiodide reagents is also made. Since THF is typically used for $SmI_2$ reactions, the reaction with 2-phenethyl iodide is carried out in THF with $TmI_2(DME)_x$ (entry 7). Analysis of the results shows comparable yields and identical selectivities to reactions conducted in DME (entry 2). However, the reaction of $SmI_2(THF)_x$/HMPA in DME gave ethylbenzene as the only product by GC (entry 8). This is consistent the report of Molander et. al. that DME is an unacceptable solvent for organosamarium reactions.

Reactions of $TmI_2(DME)_x$ with other alkyl halides are also investigated, Scheme 2. As shown in Table 2, the reaction of MeI with two equivalents of $TmI_2(DME)_x$ in DME lead to 99% conversion to products with a ratio of axial α-4-tert-butyl-1-methyl-cyclohexanol and to equatorial β-4-tert-butyl-1-methyl-cyclohexanol of 64:36 (entry a). The reaction of n-butyl iodide (entry b) gave a 99% conversion to product with a ratio of axial α-4-tert-butyl-1-butyl-cyclohexanol and to equatorial β-4-tert-butyl-1-butyl-cyclohexanol of 74:26. Compounds α-4tert-butyl-1-butyl-cyclohexanol and β-4-tert-butyl-1-butyl-cyclohexanol can also be obtained from reactions of n-butyl bromide and chloride in yields of 96% and 97%, respectively (entries c and d). The product ratios are the same as for the n-butyl iodide reaction. Reactions using the Barbier procedure (entry e) in which $TmI_2(DME)_x$ is added to a mixture of the ketone and the alkyl halide gave significantly lower yields of coupled products and generated 4-tert-butylcyclohexanol, a product resulting from the reduction of the ketone. This is consistent with the expected high reactivity of Tm(II) compared to Sm(II) with ketones.

Since $TmI_2(DME)_x$ exhibits such high reactivity at room temperature, its viability at reduced temperature is examined. In these reactions, $TmI_2(DME)_x$ is added as a DME solution by syringe using a saturated stock solution generated in situ from Tm and $I_2$. Phenethyl iodide reacts smoothly at −22° C. in 10 minutes to form phenethylcyclohexanol in 96% yield (entry f). The reaction of phenethyl bromide with cyclohexanone at 0° C. produces a 96% yield of phenethylcyclohexanol in 20 minutes (entry g), while reaction at −22° C. gave a 94% yield in 60 minutes (entry h). Phenethyl chloride reacts at 0° C. to give a 90% yield after 1 hour (entry j). This variation of reaction time as a function of temperature could be used to control regiochemistry in sequenced reactions.

Encouraged by these results, we examine the possibility of accomplishing this $TmI_2$ reactivity exclusively in THF, since it may be desirable to avoid DME in some situations. As shown in entries k–m, $TmI_2(THF)_x$ generates conveniently in situ in THF as a stock solution on a Schenk line from Tm and $I_2$, gave excellent results as well. On the basis of these results, $TmI_2$ has the potential to be an effective replacement for $SmI2(THF)_x$ when HMPA is to be avoided, when the $SmI_2(THF)_x$/HMPA system is too weak a reductant to accomplish a reaction, when sub-ambient reaction temperatures are desirable, and when reactions faster than those achievable via $MX_2$ and samarium addition and photolysis are needed. The higher reactivity of $TmI_2$ may limit its functional group tolerance in some applications, but it is possible that this can be overcome by developing the appropriate protocols.

There are many advantages for using Thulium diiodide $(DME)_3$ according to this invention as a catalyst to add alkyl groups to organic substrates For example, the starting material for the alkylation process may be alkyl bromide and alkyl chloride reagents instead of the usual and more expensive alkyl iodides. Additionally, it is safer, especially for the production of pharmaceutics. For example, since Kagan's seminal studies in 1977, samarium diiodide has become a popular reducing agent in organic synthesis. In many cases, reactivity may be enhanced by adding hexamethylphosphoramide (HMPA) to $SmI_2(THF)_x$. Unfortunately, this most effective and popular additive may be highly carcinogenic and alternatives are highly desirable.

The following schemes 1 and 2 shows TmI$_2$ catalyzing the reaction of an alkyl halide with 4-tert-butylcyclohexanone to give α-tert-butyl-1-phenethyl-cyclohexanol, and β-tert-butyl-1-phenethyl-cyclohexanol; and TmI$_2$ (DME)$_2$ catalyzing an alkyl halide with 4-tert-butylcyclohexanone to give α-4-tert-butyl-1-methyl-cyclohexanol, β-4-tert-butyl-1-methyl-cyclohexanol, α-4-tert-butyl-1-butyl-cyclohexanol and β-4-tert-butyl-1-butyl-cyclohexanol.

Scheme 1

The reaction of 2-phenethyl halides with 4-tert-butylcyclohexanone

Scheme 2

The reaction of methyl iodide and n-butyl halides with 4-tert-butylcyclohexanone (RX = MeI, n-BuI, n-BuBr, n-BuCl)

R = Me   α-4-tert-butyl-1-methyl-cyclohexanol
R = Bu   α-4-tert-butyl-1-butyl-cyclohexanol β-4-tert-butyl-1-methyl-cyclohexanol
β-4-tert-butyl-1-butyl-cyclohexanol

TABLE 1

Comparison of Reactivity of TmI$_2$(DME)$_x$ and SmI$_2$(THF)$_x$/HMPA at 25° C.

| Reagent | Alkyl halide | Solvent | Time[a] | Yield[b], (ax:eq[c]) |
|---|---|---|---|---|
| 1. SmI$_2$(THF)$_x$/HMPA | PhCH$_2$CH$_2$I | THF | <1 min | 92% (77:23) |
| 2. TmI$_2$(DME)$_x$ | PhCH$_2$CH$_2$I | DME | <1 min | 99% (79:21)[d] |
| 3. SmI$_2$(THF)$_x$/HMPA | PhCH$_2$CH$_2$Br | THF | 15 min | 65% (77:23) |
| 4. TmI$_2$(DME)$_x$ | PhCH$_2$CH$_2$Br | DME | <1 min | 92% (79:21)[d] |
| 5. SmI$_2$(THF)$_x$/HMPA | PhCH$_2$CH$_2$Cl | THF | 18 h | (no reaction) |

TABLE 1-continued

Comparison of Reactivity of TmI$_2$(DME)$_x$ and SmI$_2$(THF)$_x$/HMPA at 25° C.

| Reagent | Alkyl halide | Solvent | Time[a] | Yield[b], (ax:eq[c]) |
|---|---|---|---|---|
| |  Cl | DME | 3 min | 95% (79:21)[d] |
| 7. TmI$_2$(DME)$_x$ |  I | THF | <1 min | 99% (79:21) |
| 8. SmI$_2$(THF)$_x$/HMPA |  I | DME | <1 min | 0% |

[a]Time elapsed until color change from characteristic Ln(II) to Ln(III); in each case the Ln(III) color changed immediately to white upon addition of the ketone.
[b]Determined by GC/MS based on unreacted ketone.
[c]Isomer ratio was determined by GC/MS.
[d]Isolated yields were obtained for entries 2 (97%), 4 (97%), and 6 (95%)

TABLE 2

Additional TmI$_2$ Reactivity: Other Substrates, Low Temperature Reactions, and TmI$_2$(THF)$_x$ Reactions in THF

| | Alkyl halide | Electrophile | Temp | Time[a] | GC Yield (ax:eq[c]) | Isolated Yield |
|---|---|---|---|---|---|---|
| | | Reactions in DME using isolated TmI$_2$(DME)$_x$ | | | | |
| a) | MeI |  | 25° C. | <1 min | 99% (64:36) | — |
| b) | n-BuI |  | 25° C. | <1 min | 99% (74:26) | 85% |
| c) | n-BuBr |  | 25° C. | <1 min | 96% (74:26) | 97% |
| d) | n-BuCl |  | 25° C. | 5 min | 97% (74:26) | 95% |
| e) | MeI[d] |  | 25° C. | <1 min | 36%[d] (68:32) | — |
| | | Reactions in DME using TmI$_2$(DME)$_x$ generated in situ | | | | |
| f) |  I |  | -22° C. | 10 min | 93% | 87% |
| g) |  Br |  | 0° C. | 20 min | 96% | 90% |

TABLE 2-continued

Additional TmI₂ Reactivity: Other Substrates,
Low Temperature Reactions, and TmI₂(THF)ₓ Reactions in THF

| Alkyl halide | Electrophile | Temp | Time[a] | GC Yield (ax:eq[c]) | Isolated Yield |
|---|---|---|---|---|---|
| h)  |  | −22° C. | 60 min | 94% | 94% |
| i)  |  | 25° C. | 3 min | 98% | 95% |
| j)  |  | 0° C. | 1 h | 90% | 85% |

Reactions using TmI₂(DME)ₓ generated in situ

| | | | | | |
|---|---|---|---|---|---|
| k)  |  | −45° C. | 40 min | 83% | 80% |
| l)  |  | −25° C. | 45 min | 87% | 83% |
| m)  |  | 25° C. | 10 min | 90% | 85% |

[a]Time elapsed until color change from characteristic Ln(II) to Ln(III); in each case the Ln(III) color changed immediately to white upon addition of the ketone.
[b]Determined by GC based on unreacted ketone.
[c]Isomer ratio was determined by GC/MS.
[d]Barbier conditions.

EXAMPLE 1

Procedures for Reactions Using Isolated TmI₂(DME)₃

Under nitrogen, a dilute solution of the alkyl iodide (0.05 mmol in 5 mL of DME) is added to an emerald green solution of TmI₂(DME)ₓ (60 mg, 0.1 mmol) in DME (4 mL) over 1–2 min. This causes the emerald green solution to become yellow-orange and a white precipitate is formed. A solution of 4-tert-butylcyclohexanone (6.25 mg, 0.05 mmol) in DME (2 mL) is added to the yellow-orange solution, which immediately became a clear solution with a white precipitate. The reaction is quenched with an aqueous solution saturated with NH₄Cl and extracted with ether pentane (1:1). The organic extracts are washed with H₂O (2□ 5 mL) and dried over MgSO₄. The crude product is analyzed by GC. Isolation of the products by flash chromatography (EtOAc:hexanes 1:9) gave a white crystalline product whose ¹H NMR. ¹³C NMR, and mass spectra are consistent with the literature values.

EXAMPLE 2

Procedure Using TmI₂(DME)ₓ Generated In Situ

To a Schlenk flask containing thulium powder (0.80 g, 4.7 mmol) and 90 mL of dry, oxygen-free DME, Iodine (1.20 g, 4.7 mmol) is added under a nitrogen purge to generate a dark brown-red solution. The flask is fitted with a reflux condenser and the solution is heated to reflux with rapid stirring. After about 2 hr the solution changes to white. Shortly thereafter (10 min) the color changes to emerald green. Heating continues until white insoluble materials are replaced by dark green product. After about 1 hr, no more white precipitate is observable and dark green TmI₂(DME)ₓ is present as a precipitate from the saturated solution. An aliquot of the saturated solution [0.05 M (determined by complexometric titration), 10 mL, 5 mmol] is then added via syringe to a solution of 0.25 mmol of the organic halide in ca. 5 mL DME in a septum-covered flask under nitrogen. Once an orange-yellow solution is formed, 0.25 mmol of the ketone is injected through the septum resulting in a clear solution with a white precipitate. The reaction is then quenched with an aqueous solution saturated with NH₄Cl and extracted with ether/pentane (1:1). The organic extracts are washed with H₂O (2×5 mL) and dried over MgSO₄. The crude product was analyzed by gas chromatography. Isolation of the products by flash chromatography gives a white crystalline product whose spectra are consistent with the literature values.

EXAMPLE 3

Procedure Using TmI₂THF)ₓ Generated In Situ in THF

To a Schlenk flask containing thulium powder (1.0 g, 5.9 mmol) and 50 mL of dry, oxygen-free THF, Iodine (1.4 g, 5.5 mmol) is added under a nitrogen purge to generate a dark brown-red solution. The flask is fitted with a reflux condenser and the solution is heated to reflux with rapid stirring. After about 20 min the solution changes to white. Shortly thereafter (10 min) the color changes to emerald green. Heating continues until white insoluble materials are replaced by dark green product. After about 1 h, no more white precipitate is observable and dark green $TmI_2(THF)_x$ is present as a precipitate from the saturated solution. An aliquot of the saturated solution [0.1 M (determined by complexometric titration), 5 mL, 5 mmol] is then added via syringe to a solution of 0.25 mmol of the organic halide in ca. 5 mL of THF in a septum-covered flask under nitrogen. Once an orange-yellow solution is formed, 0.25 mmol of the ketone is injected through the septum resulting in a clear solution with a white precipitate. The reaction is then quenched with an aqueous solution saturated with $NH_4Cl$ and extracted with ether/pentane (1:1). The organic extracts are washed with $H_2O$ (2×5 mL) and dried over $MgSO_4$. The crude product was analyzed by gas chromatography. Isolation of the products by flash chromatography gives a white crystalline product whose spectra are consistent with the literature values.

As the chemistry of Thulium diiodide $(DME)_3$ becomes more important it may be necessary to explore in detail the synthesis and structure of Thulium diiodide $(DME)_3$. As discussed above, to date this important divalent 4f element chemistry has involved only three metals, Sm(II), Eu(II), and Yb(II). Divalent ions can be formed for all of the metals in the 4f series by high-temperature reduction of the halides with the metal or by radiolysis of trivalent metal ions trapped in crystalline lattices, but these insoluble and dilute systems are generally only characterized by spectroscopic means. The large reduction potentials (−2.3 to −2.9V Ln(III)/Ln(II)) for 4f elements other than Eu, Yb, and Sm make these other divalent metals difficult to isolate as molecular species. Two exceptions are in the literature $[\{K(monoglyme)\}_2\{(C_8H_8)_2Ce\}]$ (monoglyme=diethyleneglycolmonoethyl ether) and $[\{(C_5Me_5)_2NdCl_2\}\{K:(THF)_n\}_2]$, but neither of these species have been fully characterized by X-ray crystallography.

We report here the first crystal structure analysis of a molecular complex of a divalent 4f element other than Eu, Sm, and Yb. This is done with thulium, which has the most stable divalent oxidation state after Eu, Yb, and Sm (Tm (III)/Tm(II)=−2.3V vs NHE) The thulium diiodide or $Tm_2(DME)_3$ (Compound C) (dme=di-methoxyethane). is synthesized by reduction of $TmI_3$, with thulium metal in refluxing DME. Repeated treatment of the solid reactants with DME, followed by removal of DME under vacuum ultimately gave a 54% yield of Compound C as an air-sensitive malachite-green crystalline solid. In the solid state and in solution, Compound C slowly decomposes at room temperature to give a colorless solid and gaseous products. Decomposition is noticeably accelerated by sunlight which will completely decolorize a 1 mM solution of Compound C in one hour, ligands are chelating and one is monodentate.

Figure 1:
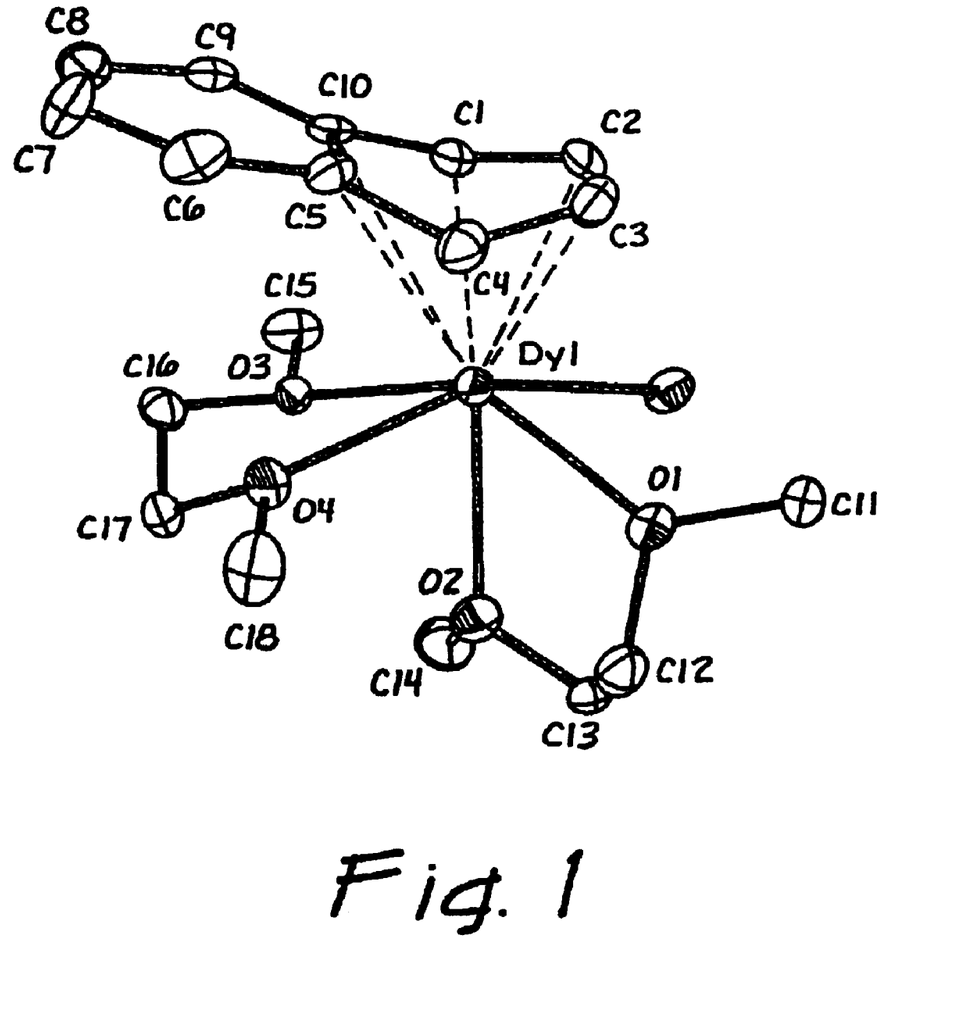
FIG. 1 is a thermal ellipsoid plot of one of the independent $TmI_2(DME)_3$ molecules in a unit cell, wherein ellipsoids are drawn at the 50% probability level.

Elemental analysis on Compound C is consistent with three DME molecules per $TmI_2$ unit. This is confirmed by an X-ray crystal structure analysis (FIG. 1). The unit cell contains two independent molecules that have similar bonding parameters. The thulium atom in $Tm_2(DME)_3$ is seven-coordinate; two DME ligands are chelating and one is monodentate. This is a rare example of a complex containing a monodenate DME ligand. The pentagonal-bipyramidal structure of Compound C is similar to those of the solvated divalent Samarium diiodide complexes, $SmI_2(THF)s$ (Compound D), $SmI_2 (DME)(THF)_3$ (Compound E) and $SmI_2(DME)_2(THF)$ (Compound F).

In all of these complexes, the halide ligands are in the axial positions and oxygen donor atoms are at the equatorial sites. The average I—Tm—I angle (174.3(5)°) in Compound C is similar to the I—Sm—I angles in Compound E and Compound F (178.8(1)°). The I—Tm—O angles range from 79.7(4) to 102.8(3)° and thus deviate from the angle expected in a perfect pentagonal bipyramid (90°). The corresponding I—Sm—O angles in Compound E and Compound F range from 79.2(1°) to 100.6(1°). The range of O—Tm—O angles for adjacent donor atoms (65.8(3)–80.5 (5)°) is also similar to the corresponding range of O—Sm—O angles (63.6(I)–80.2(2)°) in Compound E and Compound F, and differs from the ideal angle of 72° because some of these angles involve a single chelating ligand and some are between ligands.

Previous data suggests that $[LnZ_2(solvate)_x]$ complexes, in which Z is an anionic ligand, favors x=5 and a pentagonal-bipyramidal structure. The structure of Compound C strongly supports these findings, since one DME molecule remains monodentate rather than binding as a bidentate ligand to form an eight-coordinate complex. Another alternative which is not observed is a six-coordinate bis(DME) complex.

In comparison with the metal-iodide distances in the Samarium(II) complexes Compound E and Compound F, the average Tm—I distance (3.16(2) Å) in Compound C is in the range expected for a Tm(II) complex. The Sm—I distances in Compound E and Compound F are 3.231(I) –3.246(I) Å, and the ionic radius of samarium is about 0.13 Å larger than that of thulium. The range of Tm—O distances (2.456(13)–2.546(14) Å) for the two independent molecules in the unit cell is wider than the range observed for Sm(II)—O(DME) distances (2.595(5)—2.646(4) Å) in Compound E and Compound F, but again these distances are consistent with the presence of Tm(II) after the difference in radius (0.13 Å) is taken into consideration.

The Tm(II)—O distances in Compound C are significantly different from the distances found in Tm(III) complexes. For example, Tm(III)—O(THF) distances of 2.353 (3) and 2.315(3) Å have been reported in eight-coordinate $[(C_8H_8)Tm\{PhC(NSiMe_3)_2\}(THF)]$ and five-coordinate $[Tm\{P(SiMe_3)_2\}_3(THF)2]$, respectively. No Tm(III)—I distances are available for comparison, but Tm(III)—Cl distances ranging from 2.585(4) to 2.667(2) Å are found in the eight-coordinate complexes $[TmCl_2(OH_2)_2([12]crown-4)]$ Cl and $[TmCl(terpy)(OH_2)_4]Cl_2.3H_2O$ (terpy=2.2':6'.2"-terpyridine). Assuming that metal-chloride distances are typically 0.31–0.42 Å shorter than metal-iodide distances, analogous Tm(III)—I distances would be in the range 2.89–3.09 Å which is substantially shorter than those observed in Compound C.

The UV/V is spectrum of Compound C is similar to that of a solution of $TmI_2$ in THF prepared by heating $TmI_3$ with thulium metal in a welded tantalum crucible under argon at 800° C. The measured effective magnetic moment of Compound C (4.53 $\mu_B$ (293 K.)) matches the value of 4.5 $\mu_B$ calculated for a $4F^{13}$ electron configuration and found for isoelectronic Yb(III) complexes. This value differs significantly from Tm(III) magnetic moments which are typically 7.1–7.5 $\mu_B$.

These data unequivocally establish the existence of a new soluble divalent 4f element system whose chemistry can be explored. The high reactivity of this complex suggests that a rich chemistry can be developed. FIG. 1 further shows a thermal ellipsoid plot of one of the independent $TmI_2$ $(DME)_3$ molecules in the unit cell of 21, wherein ellipsoids are drawn at the 50% probability level. Selected bond lengths (Å) are: TmI—O5 2.47 (2), TmI—O1 2.48 (2), TmI—O2 2.489 (14), TmI—O3 2.50 (2), TmI—O4 2.50 (2), TmI—I1 3.141 (2), TmI-I2 3.186 (2); Selected angles (°) are: O5-TmI—O2 73.3 (5), O1-TmI—O2 65.8 (5), O5-TmI—O3 80.1 (5). O1-TmI—O4 75.9 (5). O3-TmI—

O4 67.9 (5). O5-TmI—I1 92.3 (4). O1-TmI—1 83.4 (4), O3-TmI—I1 83.8 (4), O4-TmI—I1 91.8 (4). O5- TmI—I2 91.2 (4). O1-TmI-12 97.7 (4), O2-TmI-12 84.6 (4), O3-TmI-12 91.5(4). O4-TmI-12 82 4 (4), I1-Tm1-I2 173.68 (6).

EXAMPLE 4

Synthesis of $TmI_2(DME)_3$

All manipulations are carried out under the exclusion of oxygen and moisture using vacuum line techniques. Thulium flings {6.2 g, 36mmol), Iodine (5.0 g, 19.7 mmol), and DME (20 mL) are stirred for 48h under vacuum at mom temperature. The $TmI_3$ that precipitates is washed with DME (5×70 mL) to remove unconverted Iodine. The remaining mixture of Tm and $TmI_3$ is treated with DME (80 mL), and the mixture is heated to reflux and stirred until the solution turned green (for about 15 to about 90 minutes, preferably about 30 to about 45 minutes). The green solution is decanted from the solid $Tm/TmI_3$ mixture. DME is transferred from the solution by condensation under vacuum back to the remaining Tm and $TmI_3$. The mixture is again heated to reflux and stirred until the solution turn green. The operation is repeated six times. Final removal of solvent from the deep green solution by condensation under vacuum at room temperature produces malachite-green crystalline solids, which are recrystallized from DME at −10° C. to yield Compound C (7.3 g, 54%). X-ray quality crystals are grown from DME at 38° C. The crystals decompose without melting on heating at 100° C. and are soluble in DME to the extent of 0.1 g/mL. IR(KBr): v=2929 s, 2879 m, 2829 w, 1453 s, 1409 w, 1364 w, 1284 w, 1239 w, 1189m, 1095 s, 1055 s, 1030 a, 861 s, 811 w, 547 w, 482 w cm$^{-1}$. UV/V is (1.15×10$^{-3}$ M in DME, 20° C., $Å_{max}(\epsilon)$): 298 (700), 416 (250), 562 (90), 624 (80) nm. Anal. calcd for $C_{12}H_{30}O_6I_2Tm$: I 36.62, Tm 24.37; found: 16.28, Tm 23.58. Magnetic susceptibility (293 K) $x_M$=8741×10$^{-6}$, $\mu_{eff}$= 4.5 $\mu_B$.

In general, the method of synthesizing the dihalogenated lanthanide complex, such as the $TmI_2(DME)_3$, according to this invention employs the step of refluxing under an inert gas, for example nitrogen, for about 30 to about 90 minutes, preferably 60 minutes. This step substantially eliminates the need for repeated vacuum transfers, providing for a simple and more efficient method of synthesizing lanthanide catalysts.

Thulium diiodide (DME)$_x$ is clearly effective as a reducing agent, for example it may catalyze an addition reaction to a carbonyl moiety of a molecule better than the presently used catalysts, such as $SmI_2$ (DME)$_x$. However, the present invention includes other lanthanide catalysts as well. For example, in another preferred embodiment, Dysprosium diiodide or Dysprosium diiodide (DME)$_x$ may also be employed as an effective lanthanide catalyst.

Divalent ions of most of the lanthanides have been reported to form under extreme conditions in solid state lattices, isolation of easily accessible, soluble forms that would be used in organic synthesis seemed unlikely. However, Bochkarev and co-workers have recently reported that a soluble Dy(II) complex can be obtained from $Dy/I_2$ reactions which occur at temperatures up to 1500° C. Although the analytical and spectroscopic data are consistent with Dy(II), the existence of this ion could not be established by magnetic data since the Dy(II) and Dy(III) ions coincidentally have the same magnetic moment and definitive structural data are elusive. Since several incorrect claims of unusual oxidation states of f element complexes have been made in the past based only on spectroscopy, we want crystallographic confirmation of the existence this ion before its use in organic synthesis is examined.

We report here the first crystallographic data on a molecular complex of Dy(II) as well as a more convenient synthesis of solid $DyI_2$ that allows it to be stored as a solid and conveniently solubilized for use in organic syntheses. We also describe some preliminary reactions that demonstrate the utility of this reagent in organic synthesis including the reduction of naphthalene.

Crystals of $DyI_2(DME)_3$, prepared by the method of Bochkarev, are grown from DME at −20° C. in a nitrogen-containing glove box over a period of 36 h. These crystals are found to be isomorphous with $SmI_2(DME)_3$. Since we are suspicious that we could actually isolate such a reactive species, the same crystal examine by X-ray diffraction is also examined by energy dispersive absorption X-ray spectroscopy (EDAX) which confirms that it is truly a dysprosium complex, $DyI_2(DME)_3$, like its samarium analog, has an unusual structure in which there are two independent molecules in the unit cell, one of which has a linear I—Dy—I component and the other which has a bent I—Dy—I moiety, FIG. 2.

Figure 2:
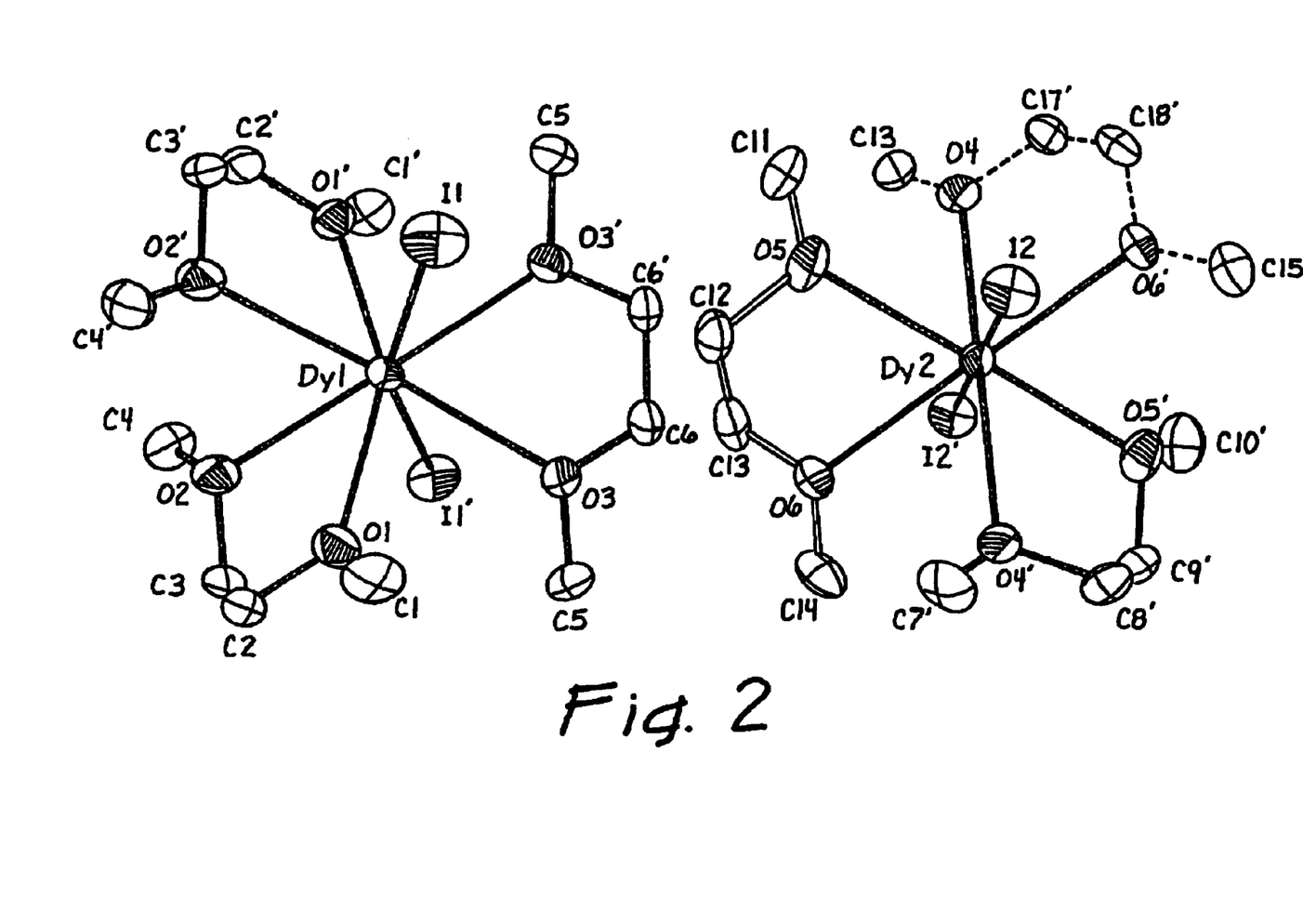
FIG. 2 is a thermal ellipsoid plot showing the structure of $DyI_2(DME)_3$ with thermal ellipsoids drawn at the 50% probability level.

FIG. 2 further shows structure of $DyI_2$ (DME)$_3$ with thermal ellipsoids drawn at the 50% probability level. The selected bond lengths (Å): Dy1-O1, 2.587(2); Dy1-O2, 2.603(2); Dy1-O3, 2.622(2) Dy1-I1, 3.2628(3); Dy2-O4, 2.585(2); Dy2-O5, 2.630(2); Dy2-O6, 2.678(21); Dy2-I2, 3.2371(3); Selected angles (°) are I1-Dy1-I1', 157.322(12); I2-Dy2-I2,' 180.000(9).

Each molecule has three chelating DME ligands that generate a hexagonal bipyramidal geometry in the linear I—Dy—I case and a distorted dodecahedral geometry in the bent I—Dy—I system. This differs from the structure of $TmI_2(DME)_3$ which contains one DME and is seven coordinate. This difference is consistent with the smaller radial size of Tm.

Once the existence of $DyI_2(DME)_3$ is crystallographically established, we sought a more convenient preparation that would allow it to be used as a routine reagent. Solid $DyI_2$ can be conveniently prepared in multi-gram quantities by reacting dysprosium filings and Iodine in an alumina or quartz crucible contained within a quartz tube connected to a Schlenk line.

EXAMPLE 5

Synthesis of $DyI_2$

In air, Dy filings (3.0 g, 18.4 mmol) are spread evenly in a layer on the bottom of a 10-mL alumina or quartz crucible. Iodine (4.75 g, 18.7 mmol) is then layered on top of the metal. The charged crucible is placed in a 20×4.5 cm quartz test tube fitted with a 55/50 joint which is connected to a trap and a Schlenk line in a well-shielded hood. The tube is evacuated and refilled with $N_2$ three times to remove oxygen. During the synthesis, the apparatus is under a nitrogen atmosphere connected to a mineral oil bubbler. The apparatus is tipped at a 60° angle to avoid directly heating the joint and the bottom of the tube containing the crucible is heated with a Meeker burner at maximum heat. The tube initially fills with $I_2$ vapor and a bright light flash indicates ignition of the metal. Heating of the initial mixture is continued at the bottom of the tube for about 2 min, during which time $I_2$ is consumed. Vacuum is then applied to transfer unreacted $I_2$ to the trap. A nitrogen atmosphere is reestablished in the vessel and heating is continued for 15 min during which time part of the mixture melts. The system is allowed to cool to room temperature and the apparatus is transferred to a nitrogen-filled glovebox. The solid mass of $DyI_2$ is removed from the crucible with a spatula and crushed with a mortar and pestle. The unreacted metal (1.25 g), which is left as a nugget, is easily identified and removed while the $DyI_2$ is being ground. $DyI_2$ (3.8 g, 85% based on metal consumed) is recovered as a violet powder suitable for synthetic reactions. Since solutions in DME or THF are light and temperature sensitive, they should be prepared immediately before use.

The solid mass of DyI$_2$ that forms can be easily separated from residual metal. The DyI$_2$ can be crushed with a mortar and pestle under an inert atmosphere and stored for long periods under nitrogen until needed.

In general the steps of the present invention allows for the initial reaction to be followed by continual heating of about 1 to about 60 minutes, preferably about 30 minutes. The continual heating in accordance with the present invention produces a melt, which completes the reaction. On the other hand, known methods of synthesis involve, for example, reactions in glass tubes which are heated with a Bunsen burner. Such methods only allows for a short reaction time (on the order of seconds).

Some of the advantages of synthesizing DyI$_2$ according to the present invention are a larger quantity of starting material (e.g. more than about 5 grams, preferably about 15 to about 20 grams) may be used and the percentage yield of the product is higher.

Although the Example 5 demonstrated one embodiment of how DyI$_2$ may be synthesized, it is possible to synthesize other lanthanide catalysts, for example TmI$_2$, using the methods as disclosed in Example 5 or modifications of such method as would be known to one of ordinary skill in the art.

Since solutions of DyI$_2$ are so reactive, they should be prepared immediately before use. DyI$_2$ may be used conveniently by making a saturated solution in THF or DME at temperatures below −20° C. The solubility of DyI$_2$ in THF is 0.025 M at −45° C. The utility of DyI$_2$(THF)$_x$ in ketone coupling reactions with alkyl halides appears to be similar to that of TmI$_2$(THF)$_x$ except that Dy(II) is much more reactive. Hence, reductions of alkyl chlorides that take 60 minutes at 0° C. with TmI$_2$(THF) and would not occur at all with SmI$_2$(THF)$_x$/HMPA, proceed immediately at −45° C. with DyI$_2$(THF)$_x$. For example, addition of 2-chloroethylbenzene to DyI$_2$(THF)$_x$ at −45° C. immediately dissipates the dark green color. After reaction with cyclohexanone an 88% isolated yield of the coupled product, phenethylcyclohexanol, is obtained (Eq. 1).

Eq. 1

It should be noted, however, that although DyI$_2$ is a strong reducing agent, it is not a strong base. For example, the addition of dry 2-propanol to a solution of DyI$_2$ in DME at 25° C. showed no color change even after 4hr. DyI$_2$ is known to react quickly under the same conditions with difficult to reduce compounds such as naphthalene, so initially this observation is surprising. This is consistent with a compound that is a strong reducing agent, but not a strong base.

Figure 3:
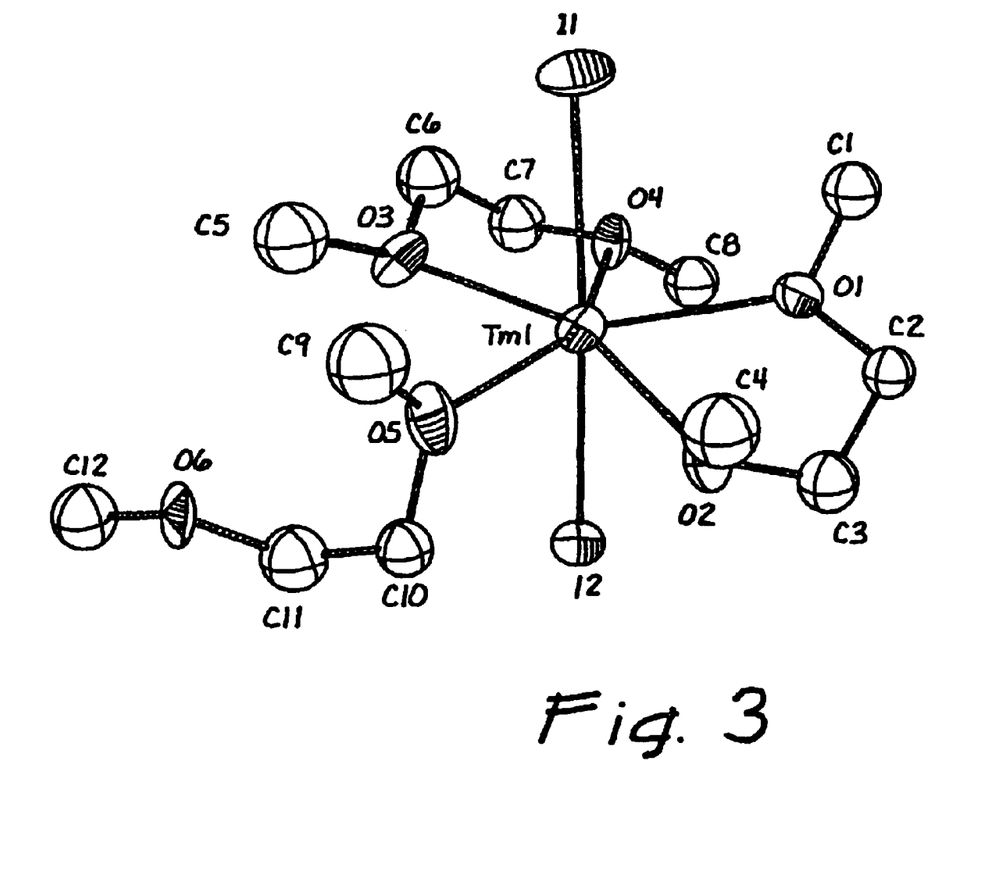
FIG. 3. Structure of $(C_{10}H_8)DyI(DME)_2$ with thermal ellipsoids drawn at the 50% probability level.

DyI$_2$ in DME is a strong enough reductant to immediately react with naphthalene at −45° C. to form a dark purple solution from which (C$_{10}$H$_8$)DyI(DME)$_2$, FIG. 3, crystallizes at −20° C. Since addition of D$_2$O generates 1,4-dideuteronaphthalene, equation 2, this reaction is equivalent to a Birch reduction.

Eq. 2

FIG. 3 shows the structure of (C$_{10}$H$_8$)DyI(DME)$_2$ with thermal ellipsoids drawn at the 50% probability level. The selected bond lengths (Å) are: Dy—O1, 2.467(3); Dy—O2, 2.562(4): Dy—O3, 2.411(3); Dy—O4, 2.430(3); Dy—C1, 2.510(5); Dy—C2, 2.599(5); Dy—C3, 2.605(5); Dy—C4, 2.486(5); Dy—C5, 2.992(5); Dy—C10, 3.002(4); Dy—I, 3.1382(4).

The isolation of a naphthalenide dianion complex is not unique in f element chemistry and several examples are known. However, in each case, these have been formed by reduction of naphthalene with an alkali metal and reaction of the alkali metal naphthalene dianion with an f element halide or by reaction of the lanthanide metal with naphthalene in liquid ammonia. This is the first case in which a low oxidation state lanthanide metal complex has reduced naphthalene directly in ethereal solvents.

DyI$_2$(DME)$_3$ alone does not appear to reduce benzene or anisoles, but it will reduce alkynes. Reduction of PhC≡CPh followed by hydrolysis forms exclusively cis-stilbene, Eq. 3.

Eq. 3

In summary, the existence of a molecular complex of Dy(II), namely DyI$_2$(DME)$_3$, has been established and a convenient protocol has been developed so that DyI$_2$ can be used like SmI$_2$(THF)$_x$ in THF or DME. Preliminary reactivity studies show that this reagent provides an option for metal-based reductions in organic synthesis that is intermediate between Birch reducing agents and Sm(II)/Tm(II) reagents. It is expected that, as in the case of SmI$_2$(THF)$_x$, the unique utility of DyI$_2$ in reductive organic synthesis will become more fully defined as this reagent is more thoroughly examined.

In another embodiment, Dysprosium diiodide may also be used to catalyze the reduction of a double bond (or triple bond) containing molecule, for example, with other double bond (or triple bond) containing molecules to form a polymer. In one embodiment, the polymerizable unit comprises ethylenically unsaturated monomers, such as: Monoolefinic hydrocarbons, i.e. monomers containing only carbon and hydrogen, including such materials as butadiene, myrcene, ethylene, propylene, 3-methylbutene-1,4-methylpentene-1, pentene-1,3,3-dimethylbutene-1,4,4-dimethylbutene-1, octene-1, decene-1, styrene and its nuclear, alpha-alkyl or aryl substituted derivatives, e.g., o-, m- or p-methyl, ethyl, propyl or butyl styrene, alpha-methyl, ethyl, propyl or butyl styrene; phenyl styrene, and halogenated styrenes such as alpha-chlorostyrene; monoolefinically unsaturated esters including vinyl esters, e.g., vinyl acetate, vinyl propionate, vinyl butyrate, vinyl stearate, vinyl benzoate, vinyl-p-chlorobenzoates, alkyl methacrylates, e.g., methyl, ethyl, propyl, butyl, octyl and lauryl methacrylate; alkyl crotonates, e.g., octyl; alkyl acrylates, e.g., methyl, ethyl, propyl, butyl, 2-ethylhexyl, stearyl, hydroxyethyl and tertiary butylamino acrylates, isopropenyl esters, e.g., isopropenyl acetate, isopropenyl propionate, isopropenyl butyrate and isopropenyl isobutyrate; isopropenyl halides, e.g., isopropenyl chloride; vinyl esters of halogenated acids, e.g., vinyl alpha-chloroacetate, vinyl alpha-chloropropionate and vinyl alpha-bromopropionate; allyl and methallyl compounds, e.g., allyl chloride, ally alcohol, allyl cyanide, allyl chlorocarbonate, allyl nitrate, allyl formate and allyl acetate and the corresponding methallyl compounds; esters of alkenyl alcohols, e.g., beta-ethyl allyl alcohol and beta-propyl allyl alcohol; halo-alkyl acrylates, e.g., methyl alpha-chloroacrylate, ethyl alpha-chloroacrylate, methyl alphabromoacrylate, ethyl alpha-bromoacrylate, methyl alpha-fluoroacrylate, ethyl alpha-fluoroacrylate, methyl alpha-iodoacrylate and ethyl alpha-iodoacrylate; alkyl alpha-cyanoacrylates, e.g., methyl alpha-cyanoacrylate and ethyl alpha-cyanoacrylate and maleates, e.g., monomethyl maleate, monoethyl maleate, dimethyl maleate, diethyl maleate; and fumarates, e.g., monomethyl fumarate, monoethyl fumarate, dimethyl fumarate, diethyl fumarate; and diethyl glutaconate; monoolefinically unsaturated organic nitriles including, for example, fumaronitrile, acrylonitrile, methacrylonitrile, ethacrylonitrile, 1,1-dicyanopropene-1,3-octenonitrile, crotononitrile and oleonitrile; monoolefinically unsaturated carboxylic acids including, for example, acrylic acid, methacrylic acid, crotonic acid, 3-butenoic acid, cinnamic acid, maleic, fumaric and itaconic acids, maleic anhydride and the like. Amides of these acids, such as acrylamide, are also useful. Vinyl alkyl ethers and vinyl ethers, e.g., vinyl methyl ether, vinyl ethyl ether, vinyl propyl ether, vinyl n-butyl ether, vinyl isobutyl ether, vinyl 2-ethylhexyl ether, vinyl-2-chloroethyl ether, vinyl propyl ether, vinyl n-butyl ether, vinyl isobutyl ether, vinyl-2-ethylhexyl ether, vinyl 2-chloroethyl ether, vinyl cetyl ether and the like; and vinyl sulfides, e.g., vinyl beta-chloroethyl sulfide, vinyl beta-ethoxyethyl sulfide and the like can also be included as can diolefinically unsaturated hydrocarbons containing two olefinic groups in conjugated relation and the halogen derivatives thereof, e.g., butadiene-1,3; 2-methylbutadiene-1,3,2,3-dimethylbutadiene-1,3; 2,3-dimethylbutadiene-1,3; 2-chlorobutadiene-1,3; 2,3-dichloro-butadiene-1,3; and 2-bromo-butadiene-1,3 and the like. Mixtures of the foregoing compounds may also be employed.

In a preferred embodiment, the polymerizable unit comprises butadiene, myrcene or other dienes. In a more preferred embodiment, the polymerizable unit comprises isoprene (2-methylbutadiene, the monomer in natural rubber). The reaction may be carried out in various solvents, for example neat, toluene, toluene with alkylaluminum, etc.

Preferably, the use of a lanthanide catalyst according to this invention, for example Dysprosium diiodide or Dysprosium diiodide $(DME)_3$, allows for the polymerization of isoprene which is substantially free from the addition of cocatalyst and activators. Preferably, the lanthanide catalyst used for the polymerization of isoprene is Dysprosium diiodide. This system offers a much simpler way to generate synthetic rubber. In another embodiment, the lanthanide catalyst according to this invention may also be employed in the synthesis of new types of elastomers. The gross physical properties of the polymers, which have been made, suggest that different types of polymers can be made by slightly changing the polymerization conditions.

Additionally, the method employing a lanthanide catalyst according to this invention to polymerize polymerizable units, for example isoprene has a distinct advantage over the current methods. For example, trivalent lanthanide compounds have been used to polymerize isoprene, but they involve at least two activators. The present method has a single component solid, for example Dysprosium diiodide or Dysprosium diiodide $(DME)_3$, which could be added to monomer to cause polymerization. The present method being simpler and better defined could be more efficient in terms of the catalyst used.

EXAMPLE 6

Use of $DyI_2$ in the Synthesis of an Elastomer

An elastomer derived from polymerizable unit such as isoprene may be synthesized according to the following method. To a vial containing a solution of 5 mL of isoprene and 5 mL dissolved in hexanes, 10 mg of $DyI_2$ is added. The suspension is allowed to stir for 8 hrs., after which a thick purple solution is formed. Evaporation of the hexanes leaves an elastomer that may be re-dissolved in hexanes. A $^{13}C$ NMR spectrum of the elastomer shows high cis-1,4-polyisoprene as the only observable product. $^{13}C$ NMR $\partial=135.2$, 125.0, 32.2, 26.4, and 23.4 ppm. Additionally, reactions of $DyI_2$ with isoprene may be carried out in the presence of $^iBu_3Al$. The reaction is conducted as above, with the addition of 2 ml $^iBu_3Al$ to the initial solution prior to the addition of $DyI_2$). An elastomer with properties similar to those above is formed. Quenching the reaction with isopropyl alcohol results in the evolution of gas, consistent with the quenching of unreacted $^iBu_3Al$.

In another broad embodiment, a reduction product is made from a process which comprises the step of combining a compound with a lanthanide catalyst, preferably $DyI_2$, according to this invention; in a preferred embodiment, the compound comprises a polymerizable unit, for example dienes, preferably isoprene, and the reduced product is a polymer. For example, the samples of polyisoprene obtained from reactions with $DyI_2$ share the property of being soluble in non-polar solvents such as hexanes or heptane. This may allow for the production of blends of polyisoprene with other soluble polymer to produce a value-added product with unique properties. In another embodiment, the catalytic lanthanide is Dysprosium diiodide $(DME)_3$.

While this invention has been described with respect to various specific examples and embodiments, it is to be understood that the invention is not limited thereto and that it can be variously practiced with the scope of the following claims.

What is claimed is:

1. A method of reducing a compound to form a reduction product, said method comprising the step of combining the compound with a lanthanide catalyst having the formula:

$$G_1-M-G_2$$

wherein;

M is either a Dysprosium or a Neodymium;

G$_1$ and G$_2$ are chemical entities independently selected from the group consisting of a halogen, an alkyl, an aryl, an NR$_2$, an OR$_2$, a PR$_2$ and an SR; wherein N is a nitrogen, O is an oxygen, P is a phosphorus and R is selected from the group consisting of an alkyl, an aryl, and a cycloalkyl from about 1 to about 20 carbon atoms.

2. A method according to claim 1 wherein G$_1$ is an Iodine.

3. A method according to claim 1 wherein G$_2$ is an Iodine.

4. A method according to claim 1 wherein G$_1$ and G$_2$ are the same halogen.

5. A method according to claim 1 wherein G$_1$ and G$_2$ are different halogens.

6. A method according to claim 1 wherein M is a Neodymium and G$_1$ and G$_2$ are iodines.

7. A method according to claim 1 wherein M is a Dysprosium and G$_1$ and G$_2$ are iodines.

8. A method according to claim 1 wherein M is complexed with at least one solvent molecule, S.

9. A method according to claim 8 wherein the solvent molecule comprises a Lewis base.

10. A method according to claim 9 wherein the Lewis base is a heteroatom donor base.

11. A method according to claim 9 wherein the Lewis base is selected from the group consisting of di-alkyl-oxy-ethanes, tetrahydrofuran, dienes, nitriles and ethers.

12. A method according to claim 9 wherein the Lewis base comprises a di-alkyl-oxy-ethane.

13. A method according to claim 9 wherein the Lewis base comprises a dimethoxyethane.

14. A method according to claim 8 wherein the complex has the general Formula B:

wherein;

M either a Dysprosium or a Neodymium;

G$_1$ and G$_2$ are chemical entities independently selected from the group consisting of a halogen, an alkyl, an aryl, an NR$_2$, an OR$_2$, a PR$_2$ and an SR; wherein N is a nitrogen, O is an oxygen, P is a phosphorus and R is selected from the group consisting of an alkyl, an aryl, and a cycloalkyl from about 1 to about 20 carbon atoms; and, S is dimethoxyethane (DME).

15. A method according to claim 14 wherein M is a Neodymium G$_1$ and G$_2$ are Iodine and S is dimethoxyethane.

16. A method according to claim 14 wherein M is Dysprosium, G$_1$ and G$_2$ are Iodine, and S is dimethoxyethane.

17. A method according to claim 1 wherein the compound is an organic compound, the lanthanide catalyst effects alkylation of the compound, and the reduction product is an alkylated organic compound.

18. A method according to claim 17 wherein the lanthanide catalyst is a Thulium diiodide.

19. A method according to claim 17 wherein the lanthanide catalyst effects alkylation of the organic compound with RJ, wherein R is an alkyl and J is a halogen selected from the group consisting of Iodine, Bromine, Chlorine and Fluorine.

20. A method according to claim 19 wherein G$_1$ and G$_2$ are Bromine.

21. A method according to claim 19 wherein G$_1$ and G$_2$ are Chlorine.

22. A method according to claim 1 wherein the compound comprises a polymerizable unit and the reduced product is a polymer.

23. A method according to claim 22 wherein the M is a Dysprosium, G$_1$ and G$_1$ are Iodine.

24. A method according to claim 22 wherein the polymerizable unit comprises isoprene.

25. A polymeric reduction product made from a process comprising the step of combining a compound which comprises a polymerizable unit with a lanthanide catalyst having the general Formula A:

wherein;

L is a lanthanide other than the Europium, Ytterbium or Samarium;

G$_1$ and G$_2$ are chemical entities independently selected from the group consisting of a halogen, an alkyl, an aryl, an NR$_2$, an OR$_2$, a PR$_2$ and an SR; wherein N is a nitrogen, O is an oxygen, P is a phosphorus and R is selected from the group consisting of an alkyl, an aryl, and a cycloalkyl from about 1 to about 20 carbon atoms.

26. A reduction product according to claim 25 wherein the M is a Dysprosium, G$_1$ and G$_2$ are Iodine.

27. A reduction product according to claim 25 wherein the polymerizable unit comprises isoprene.

28. A method for making a dihalogenated lanthanide compound, said method comprising the steps of:

combining a Dysprosium metal with a halogen;

reacting the Dysprosium metal with the halogen to form an initial mixture; and heating the initial mixture for about 1 to about 60 minutes.

29. A method according to claim 28 wherein the halogen is selected from the group consisting of Iodine, Bromine, Chlorine and Fluorine.

30. A method according to claim 28 wherein the halogen is Iodine.

31. A method according to claim 28 wherein the heating is for about 2 to about 30 minutes.

32. A method according to claim 28 wherein the halogen is selected from the group consisting of Iodine, Bromine, Chlorine and Fluorine.

33. A method according to claim 28 wherein the halogen is Iodine.

34. A method according to claim 28 wherein the solvent molecule S comprises a Lewis base.

35. A method according to claim 28 wherein the Lewis base is selected from the group consisting of di-alkyl-oxy-ethanes, tetrahydrofuran, dienes, nitriles and ethers.

36. A method according to claim 28 wherein the Lewis base comprises a dimethoxyethane.

37. A method of reducing a compound to form a pollmeric reduction product, said method comprising the step of combining the compound which comprises a polymerizable unit with a lanthanide catalyst having the formula:

wherein;

M is a lanthanide other than the Europium, Ytterbium or Samarium;

$G_1$ and $G_2$ are chemical entities independently selected from the group consisting of a halogen, an alkyl, an aryl, an $NR_2$, an $OR_2$, a $PR_2$ and an SR; wherein N is a nitrogen, O is an oxygen, P is a phosphorus and R is selected from the group consisting of an alkyl, an aryl, and a cycloalkyl from about 1 to about 20 carbon atoms.

38. A method according to claim 37 wherein M is selected from the group consisting of Thulium, Dysprosium, Neodymium, Cerium, Praseodymium, Gadolinium, Terbium, Holmium, Erbium, Lutetium, Lanthanum and Yttrium.

39. A method according to claim 37 wherein the M is a Thulium.

40. A method according to claim 37 wherein the M is a Dysprosium.

41. A method according to claim 37 wherein the M is a Neodymium.

42. A method according to claim 37 wherein $G_1$ is an Iodine.

43. A method according to claim 37 wherein $G_2$ is an Iodine.

44. A method according to claim 37 wherein $G_1$ and $G_2$ are the same halogen.

45. A method according to claim 37 wherein $G_1$ and $G_2$ are different halogens.

46. A method according to claim 37 wherein M is a Thulium and $G_1$ and $G_2$ are iodines.

47. A method according to claim 37 wherein M is a Dysprosium and $G_1$ and $G_2$ are iodines.

48. A method according to claim 37 wherein M is complexed with at least one solvent molecule, S.

49. A method according to claim 48 wherein the solvent molecule comprises a Lewis base.

50. A method according to claim 49 wherein the Lewis base is a heteroatom donor base.

51. A method according to claim 49 wherein the Lewis base is selected from the group consisting of di-alkyl-oxy-ethanes, tetrahydrofuran, dienes, nitrites and ethers.

52. A method according to claim 49 wherein the Lewis base comprises a di-alkyl-oxy-ethane.

53. A method according to claim 49 wherein the Lewis base comprises a dimethoxyethane.

54. A method according to claim 48 wherein the complex has the general Formula B:

wherein;

M is a lanthanide other than the Europium, Ytterbium or Samarium;

$G_1$ and $G_2$ are chemical entities independently selected from the group consisting of a halogen, an alkyl, an aryl, an $NR_2$, an $OR_2$, a $PR_2$ and an SR; wherein N is a nitrogen, O is an oxygen, P is a phosphorus and R is selected from the group consisting of an alkyl, an aryl, and a cycloalkyl from about 1 to about 20 carbon atoms; and, S is dimethoxyethane (DME).

55. A method according to claim 54 wherein M is Thulium, $G_1$ and $G_2$ are Iodine and S is dimethoxyethane.

56. A method according to claim 54 wherein M is Dysprosium, $G_1$ and $G_2$ are Iodine, and S is dimethoxyethane.

57. A method according to claim 37 wherein the compound is an organic compound, the lanthanide catalyst effects alkylation of the compound, and the reduction product is an alkylated organic compound.

58. A method according to claim 57 wherein the lanthanide catalyst is a Thulium diiodide.

59. A method according to claim 57 wherein the lanthanide catalyst effects alkylation of the organic compound with RJ, wherein R is an alkyl and J is a halogen selected from the group consisting of Iodine, Bromine, Chlorine and Fluorine.

60. A method according to claim 59 wherein $G_1$ and $G_1$ are Bromine.

61. A method according to claim 59 wherein $G_1$ and $G_2$ are Chlorine.

62. A method according to claim 59 wherein the M is a Dysprosium, $G_1$ and $G_2$ are Iodine.

63. A method according to claim 59 wherein the polymerizable unit isoprene.

* * * * *